United States Patent [19]

Martin, Jr.

[11] Patent Number: 5,640,971
[45] Date of Patent: Jun. 24, 1997

[54] BACK MOVEMENT MONITOR AND WARNING DEVICE

[76] Inventor: Robert LeRoy Martin, Jr., 1365 45th Ave. #3, Capitola, Calif. 95010

[21] Appl. No.: 458,273

[22] Filed: Jun. 2, 1995

[51] Int. Cl.⁶ ............................................. A61B 5/103
[52] U.S. Cl. ............................................ 128/781; 128/782
[58] Field of Search .................................. 128/782, 781, 128/649, 774, 835, 98.1, DIG. 25; 340/573, 689; 606/191

[56] References Cited

U.S. PATENT DOCUMENTS

| | | | |
|---|---|---|---|
| 4,290,420 | 9/1981 | Manetta | 600/29 |
| 4,436,099 | 3/1984 | Raftopoulos | 128/782 |
| 4,730,625 | 3/1988 | Fraser et al. | 128/781 |
| 4,871,998 | 10/1989 | Chaillou | 340/573 |
| 4,914,423 | 4/1990 | Fernandez | 340/573 |
| 4,958,145 | 9/1990 | Morris | 340/689 |
| 4,986,280 | 1/1991 | Marcus et al. | 128/782 |
| 5,146,929 | 9/1992 | Sawhill | 128/781 |
| 5,188,121 | 2/1993 | Hanson | 128/782 |
| 5,269,767 | 12/1993 | Wilk | 606/204.25 |
| 5,291,901 | 3/1994 | Graf | 128/782 |
| 5,337,758 | 8/1994 | Moore et al. | 128/782 |
| 5,398,697 | 3/1995 | Spielman | 128/782 |
| 5,400,800 | 3/1995 | Jain et al. | 128/782 |
| 5,402,107 | 3/1995 | Rencavage | 128/782 |
| 5,474,086 | 12/1995 | McCormick et al. | 128/782 |
| 5,474,088 | 12/1995 | Zaharkin et al. | 128/782 |

FOREIGN PATENT DOCUMENTS 2205039  11/1988  United Kingdom.

*Primary Examiner*—Guy V. Tucker
*Assistant Examiner*—Patrick W. Rasche
*Attorney, Agent, or Firm*—Michael I. Kroll

[57] ABSTRACT

A device for monitoring the flexion, extension, and rotation of a user's torso. An upper and a lower sensing arm extend vertically in opposite directions from a measuring and control box that is held about the midsection by a belt, and both arms are spring biased to hold them against the user's back. The torso engaging portions of each of the sensing arms are curved to cup the engaged portion of the anatomy and thus allows for the sensing of torso rotation due to a pair of protrusions integral to the sensing arms and ensconced within the control box. Both arms are telescopically adjustable to allow the device to be fit to differently sized people and the amount of flexion, extension, and rotation that is allowed by the device before a warning tone is sounded is adjustable.

10 Claims, 4 Drawing Sheets

BACK MOVEMENT MONITOR AND WARNING DEVICE

BACKGROUND OF THE INVENTION

This invention was disclosed in Information Disclosure Document No. 326,496, filed with the United States Patent and Trademark Office on Mar. 12, 1993 and is related to U.S. patent application Ser. No. 08/138,426 filed Oct. 20, 1993 now abandoned.

1. Field of the Invention

The present trend in medicine is preventive treatment. If one can prevent an injury before it occurs, the difficult and painful recuperation from that injury will never be necessary. The present invention seeks to prevent injury, or re-injury, by providing the user with a warning when a posture likely to cause problems occurs. The invention relates to devices that react to the movement of the wearer. More specifically, it relates to a device that is mounted on a belt and generates a progression of audible tones that correspond with the flexion, extension, and rotation of the user's torso. Even more specifically, it relates to a device where a preset range of movement can be set or programed into such a device, and if this range or limit is exceeded, the apparatus will set off a warning tone that will vary according to the type of movement, either extension, flexion, or rotation, that activated the alarm.

2. Description of the Prior Art

Back injuries are a common occurrence. In many cases, surgery is required to alleviate the distressing symptoms that can make the injured person's life a misery. Additionally, poor posture can exacerbate not only a preexisting condition, but can lead to other health problems in and of itself. There have been a number of patents issued for devices worn by the user that address this issue by generating warning tones when poor posture is sensed by the device.

U.S. Pat. No. 4,914,423 issued on Apr. 13, 1990 to Luis C. Fernandez discloses a posture improving device. This apparatus senses the expansion of the user's waist and sounds an alarm when this occurs. Contrast this to present applicant's invention which has a pair of vertically oriented arms for sensing the degree of flexion, extension, and rotation of the user's back.

In U.S. Pat. No. 4,871,998 issued on Oct. 3, 1989 to Michel B. Chaillu there is disclosed a posture belt wherein an alarm is sounded according to the distension of the belt. Again, as above, this device does not show the extended sensing arms disclosed in applicant's present application, nor does it teach a means for pre-setting the device to customize the amount of flexion or extension permitted before the alarm sounds.

Next is U.S. Pat. No. 4,730,625 issued on Mar. 15, 1988 to Gregory A. Fraser et al. wherein a posture monitoring system is described. In this device, pockets are sewn into a T-shirt, or other similar snug upper body garment, and elongated strips comprised of semiconductor strain gauges are inserted therein. The strain gauges produce an electrical signal that is monitored by an electronic circuit and, if a predetermined limit is passed, an alarm sounds. In contrast to applicant's invention, there are no extended arms, nor can the device be set to specific directions and/or degrees of allowable movement.

Another patent of interest is U.S. Pat. No. 4,958,145 issued on Sep. 18, 1990 to James A. Morris. In this device, there is disclosed a back incline indicator wherein a gravity operated mercury switch and a beeper is used to indicate when a certain preset angle from the vertical has been reached or exceeded. As in the other patents described above, there are no vertical extension arms for movement sensing, nor are indicators of torso rotation allowed for or taught in this publication.

None of these patents, or any other inventions known, taken singly or in combination, show the concept of the present invention which is the monitoring of excessive spinal cord deflections, either in compression, tension, torsion or bending, and the generation of appropriate warning signals upon the detection of a present excessive deflection.

None of the above inventions and patents, taken either singly or in combination, is seen to describe the instant invention as claimed.

SUMMARY OF THE INVENTION

The present invention is a device for monitoring the flexion, extension, and rotation of a user's torso. An upper and a lower sensing arm extend generally vertically in opposite directions form a measuring and control box that is held about the midsection by a belt. Both arms are spring biased to hold them against the user's back. The torso engaging portions of each of the sensing arms are curved to cup the engaged portion of the anatomy and this allows for the sensing of torso rotation due to a pair of protruding contacts integral to the sensing arms and ensconced within the control box. Both arms are telescopically adjustable to allow the device to be custom fitted to differently sized people and the amount of flexion, extension, and rotation that is allowed by the device before a warning tone is sounded is adjustable.

Accordingly, it is a principal object, advantage, and feature of the invention to provide a torso flexion and rotation monitor that will emit an audible tone if the user exceeds a preset angle of torso flexion, extension, or rotation.

It is another object, advantage, and feature of the invention to provide a torso monitor that includes a pair of upwardly and downwardly extending sensing arms that are telescopically adjustable, to allow differently sized people to utilize the unit.

It is a further object, advantage, and feature of the invention to provide a torso monitor wherein the torso engaging portion of the sensing arms are smoothly curved to allow for torque caused by the rotation of the torso to be transmitted to sensors within the control box.

Still another object, advantage, and feature of the invention is to provide a torso monitor wherein the telescopically adjustable arms are spring biased, such that they are held in contact with the user's body at a desired contact location regardless of normal movements of the body.

Still yet another object, advantage, and feature of the invention is to provide a torso monitor wherein the amount of flexion, extension, and rotation that is permitted before the alarm sounds is adjustable separately for both sensing arms and for both right and left torso rotation.

It is a general goal of the invention to provide improved elements and arrangement thereof in a device for the purposes described, which is inexpensive, dependable and fully effective in accomplishing its intended purposes.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein.

Similar reference characters denote corresponding features consistently throughout the attached drawings.

DETAILED DESCRIPTION OF THE PREFERRED EMBODIMENTS

Figure 1:
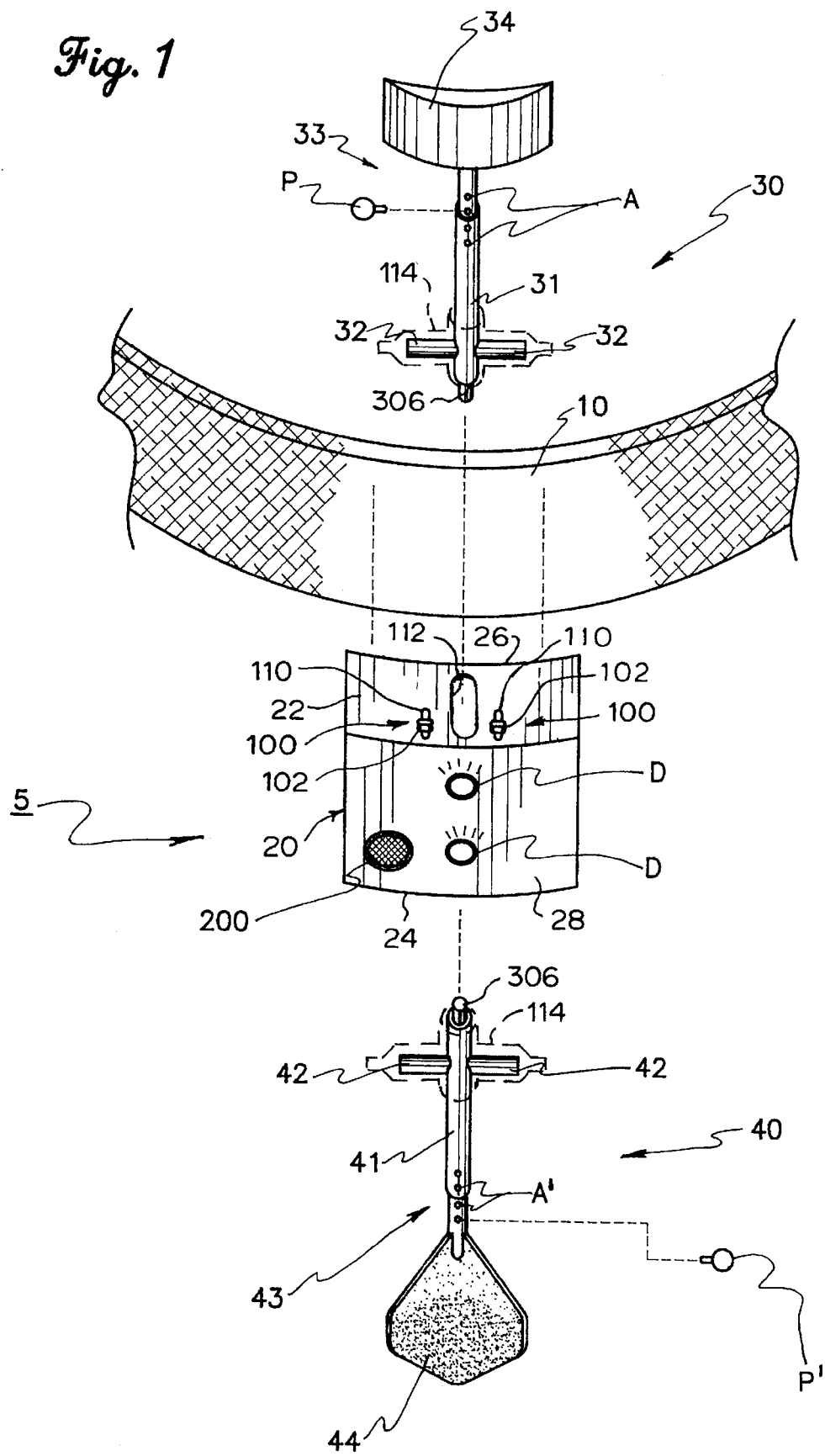
FIG. 1 is a diagrammatic exploded environmental perspective view of the present invention showing the details of the sensing arms.

Turning now descriptively to the drawings, in which similar reference characters denote similar elements throughout the several views, FIGS. 1 through 4 illustrate the present invention being a back movement and warning device indicated generally at 5. The major components of the device 5 are a belt 10, a control box 20, an upper extending movement sensing arm 30, a lower extending sensing arm 40, and a protective cover 50 that is used to keep the settings (discussed hereinafter) from being inadvertently jarred and thereby changed through contact with the user's clothing or the like.

The upper and lower sensing arms 30, 40 will be discused first. Referring to FIG. 1, the upper sensing arm 30 has an upper arm main shaft 31, two laterally extending upper rotational sensing protrusions 32, an adjustment facility 33, in this embodiment consisting of a removable pin P and a plurality of apertures A disposed along the main shaft 31, and a first torso engaging portion 34.

The lower sensing arm 40 has a lower arm main shaft 41, two laterally extending lower rotational sensing protrusions 42, an adjustment facility 43, consisting (as above) of a removable pin P' and a plurality of apertures A' disposed along the lower arm main shaft 41, and a second torso engaging portion 44.

Both adjustment facilities 33 and 43 allow the device 5 to be fitted to persons of various sizes, by altering the distance which the torso engaging portions 34, 44 are disposed from the control box 20. It should be understood that, although cooperating pins P, P' and apertures A, A' are used in this discussion, a number of other well known structures could be utilized to accomplish the same purpose. A telescopic friction assembly, for example, could be used without departing from the spirit of the claimed invention.

The first torso engaging portion 34 and the second torso engaging portion 44 are now discussed. The first torso engaging portion 34 is a slightly curved strap that allows it to engage the upper portion of the user's torso, while the second torso engaging portion 44 is shown herein as a generally triangular paddle-like member that also is slightly curved laterally, to engage the lower portion of the torso. These shapes and mounting positions have been found to be the preferred shapes and positions for the engaging portions 34, 44, but it should be noted that other shapes could serve the same purpose and would readily occur to those of ordinary skill in the art, under varying circumstances. For example, though the device 5 is shown in the figures that it can be engaged with the back of a user, it should be pointed out that the device could quite easily be fit to the user's front (the stomach and abdominal area) if desired, to monitor exercises such as "abdominal crunches" and the like.

Both the first and second torso engaging portions 34, 44 would have thereon some sort of soft padding (not shown) to provide comfort, while the device 5 is worn, and to prevent irritation over prolonged periods of use. Additionally, it is contemplated that these engaging portions 34, 44 could be constructed from a material that could be molded into different degrees of curvature or shapes to fit the user's anatomy. These types of materials, that can be bent or twisted and then maintain the configuration until force is again applied, are well known, and it is not considered necessary to discuss the minutiae of their composition. The upper and lower sensing arms 30, 40 would preferably be made of a light weight material with sufficient strength to prevent damage if they were accidentally struck. A variety of high impact plastics are available that would suit the purpose, as would a light weight metal such as aluminum.

Figure 4:
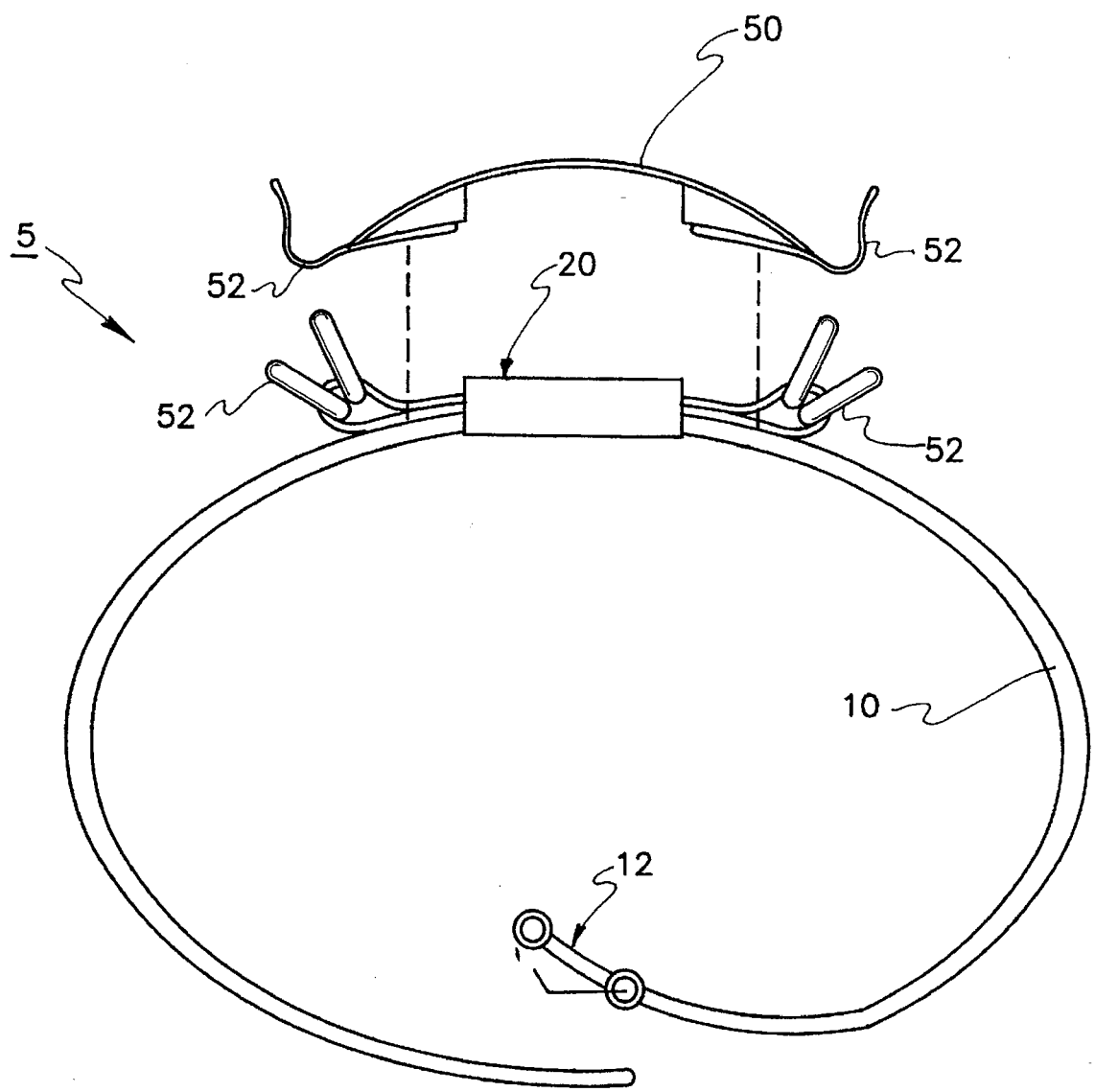
FIG. 4 is a diagrammatic top view of the device, showing the protective cover and how it fits over and on both sides of the control box, to prevent inadvertent movement of the alarm settings.

The belt 10 would be made of nylon, or like material, and it could contain a portion of elastic material to ensure a snug fit. The belt, as shown in FIG. 4, has a clasp or catch 12, to allow easy donning and doffing of the device 5 and also includes a component for removable engagement with both the protective cover 50 and the control box 20, as will be discussed hereinafter.

Figure 2:
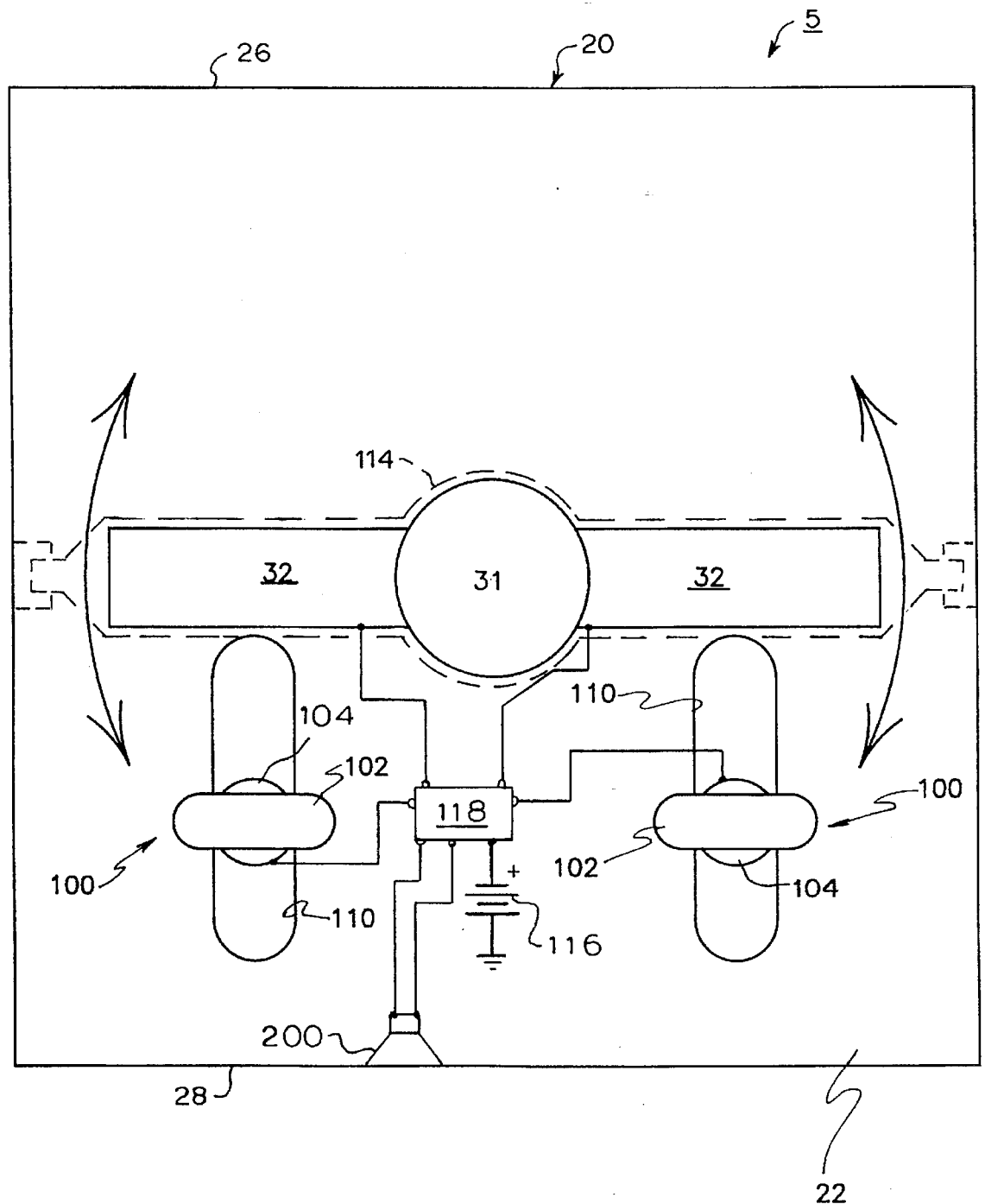
FIG. 2 is a diagrammatic partial cutaway top view of the control box, showing the laterally extending rotational sensing protrusions and the rotational adjustment sliders.
Figure 3:
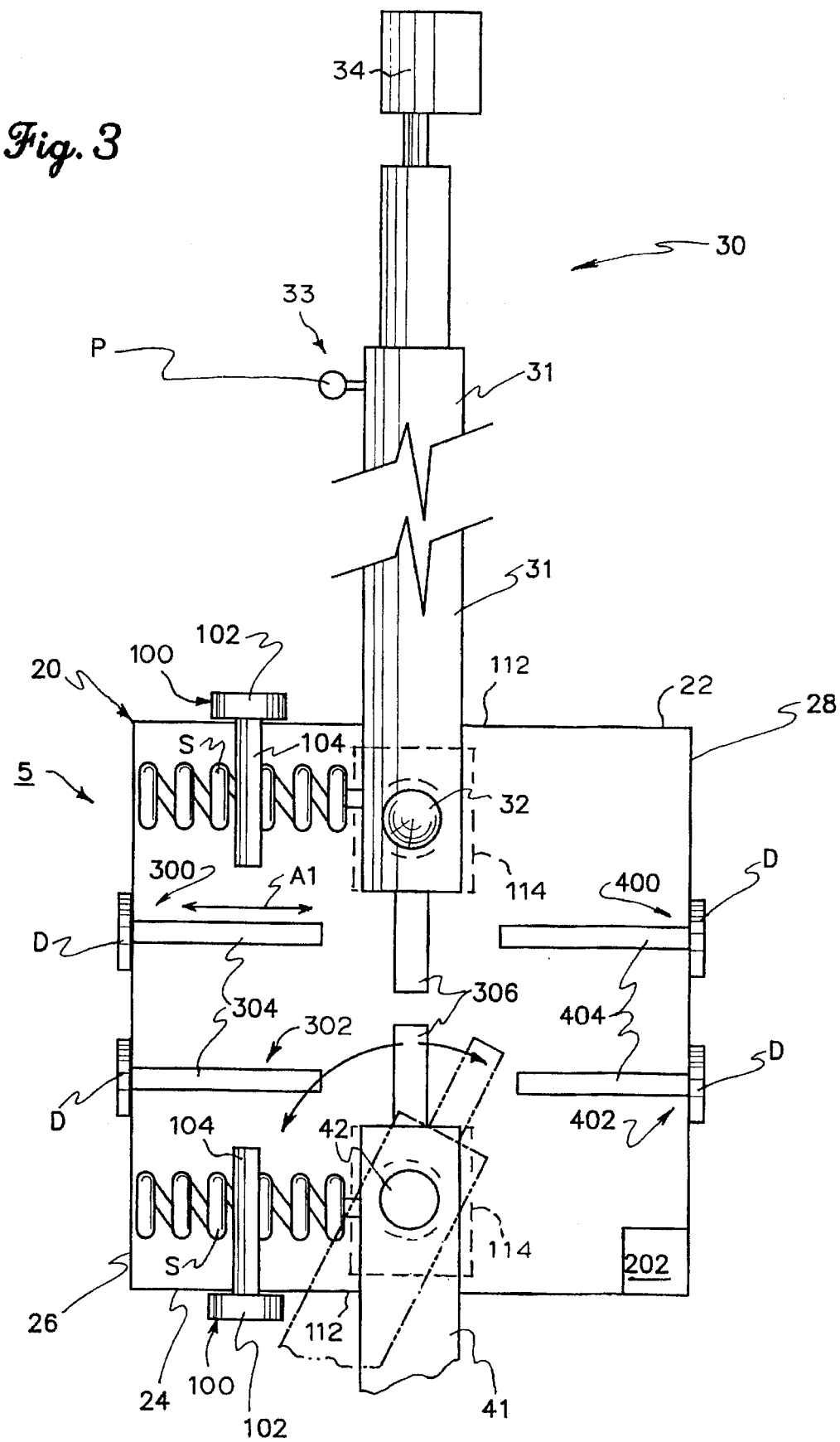
FIG. 3 is a diagrammatic cutaway side view, showing the flexion and extension sensing adjustment units and the spring biasing of both the sensing arms.

Turning now to FIGS. 2 and 3, a unit for adjustment of the allowed limits of motion and a unit for activating the appropriate alarms are discussed. It should be emphasized at the outset of this section that this is only one electromechanical method of sensing movement and activating an alarm, and in no way is intended to limit the scope of the present invention.

The rotation sensor will be discussed first. In FIG. 2, there is shown the laterally extending upper rotational sensing protrusions 32 of the upper extending sensing arm 30. This is a top view shown here, but it should be understood that the bottom of the device 5, is substantially similar as regards the rotational sensing protrusions 42 that would be seen in an analogous view thereof.

Sensing arm 30 passes through an oblong opening 112 in a top wall 22 of the control box 20. The oblong opening 112 allows the sensing arm 30 to move forward and backward. A holding piece 114 fits around a base of the upper arm main shaft 31, to provide axis of rotation, flexion and extension, which it freely allows in all planes of movement. The holding piece 14 is set inside the control box 20. It spins forward and backwards, providing flexion and extension axis. the upper arm main shaft 31 spins within the holding piece 114, which provides the axis of rotation. This puts the axis of movement in the right place for flexion, extension and rotation, while still allowing necessary movements of the sensing arm 30 and rotation of the sensing protrusions 32.

Disposed along the top wall 22 of the control box 20 are sliders 100. The sliders 100 consist of finger grips 102 and rotational contact extension members 104 that extend a sufficient distance into the control box 20, to allow contact with the rotational sensing protrusions 32, 42 of the upper and lower extending sensing arms 30, 40. The sliders 100 are adapted and configured so that they slide smoothly in cooperating slots 110 that extend through the top wall 22 and a bottom wall 24 of the control box 20. Thus upper and lower torso limits of rotation can be separately set, as well as separate right and left limitations thereof. For example, a larger amount of rotation to the right could be allowed before the alarm sound by adjusting the appropriate sliders 100 accordingly.

The rotational sensing protrusions 32, 42 and the contact extension members 104 constitute ends of an incomplete rotations alarm circuit. If the rotational contact extension members 104 and the rotational sensing protrusions 32, 34 make contact, the rotation alarm circuit is complete, and an alarm sounds over a speaker 200 contained within the control box 20. One way this conventional electrical circuit could be designed is to electrically connect a power supply, such as a dry cell battery 116, through a control unit 118 to speaker 200. The control unit 118 also has wires to the contacting elements of the mechanism such as 32 and 104. The control unit 118 acts to provide a tone pulse to speaker 200, when the appropriate contact elements are short circuited together. It is contemplated that three different sounds would be produced, depending on which of the three (rotation, extension, or flexion) preset limitations were exceeded. In this case, rotation, a series of short tones in sequence could be triggered.

Next will be flexion and extension sensing units and alarm initiation. Though these two are similar, for clarity they will be treated separately due to the different circuits and alarm tones involved. Referring now to FIG. 3, the upper and lower flexion sensing adjustment units 300 and 302 are shown. These are located on the rear wall 26 of the control box 20 and consist of adjusting dials D. The dials are similar in all four of the adjustments for the flexion and extension sensing units. The flexion sensing adjustment units 300 and 302 also include flexion contact extension members 304. The dials D are turned and through threaded components (not shown) or other well-known structures, the flexion contact extension members are moved inwardly or outwardly relative to the rear wall 26 of the control box 20, as indicated by the arrow A1.

The dials D could be calibrated and provided with indicia (not shown) that would allow the user to easily preset the degree of upper and lower flexion to be permitted. The upper and lower extending sensing arms 30, 40 have each thereon a flexion/extension protruding member 306. In the case that this member 306 comes into contact with either of the flexion contact extension members 304, a flexion alarm circuit is completed that sounds a flexion alarm through the speaker 200. It is contemplated, as discussed above, that this alarm would be differential from the rotational and extension alarms. In this case, a persistent high pitched tone could be generated.

Still referring to FIG. 3, upper and lower extension sensing adjustment units 400, 402 are shown proximate the front wall 28 of the control box 20. These consist of the dials D, that operate in the same manner discussed herein above, and extension contact members 404. In a manner similar to the flexion contact members 304 discussed above, they can be adjusted by the dials D to extend a predetermined distance into the control box 20 such that if flexion/extension protruding ember 306 comes into contact with either of the extension contact members 404, an extension contact alarm circuit is completed and an extension alarm is sounded through speaker 200. In this case, a persistent low tone could be generated.

Power would be provided for the speaker and the audible alarm circuits by a power source 202. This would preferably be in the form of easily replaceable batteries (not shown). Both the upper and lower extending sensing arms 30, 40 are biased by springs S that tend to resiliently press them against the user's torso, to provide both snug contact and accurate position sensing.

The routinist will recognize numerous other ways of alerting the user to the fact that a predetermined range of motion has been exceeded. For example, a vibrating pad (not shown) could be used proximate the belt 10, to warn the user of the device 5 that a comprised position has been reached. Alternatively, headphones could be worn to allow the user to hear the generated alarm tones.

The protective cover 50, shown in FIG. 4, is used after the motion limit ranges have been set by the user, a therapist, or the like. The cover 50 is attached by hook and loop type fastener 52 to the belt 10, to substantially cover the exposed slider finger grips 102 and dials D on the control box 20. The cover 50 is preferably padded, to prevent dislodgement of the adjustments and to increase comfort for the wearer. It is also contemplated that the control box 20 would be removable from the belt 10, for ease in setting the various adjustments for movement limitations.

LIST OF REFERENCE NUMBERS

A apertures
D adjusting dials
P pin
S springs
A' apertures
P' pin
A1 directional arrow
5 back movement monitor and warning device
10 belt
12 belt clasp or catch
20 control box
22 control box top wall
24 control box bottom wall
26 control box rear wall
28 control box front wall
30 upper sensing arm
31 upper arm main shaft
32 upper rotational sensing protrusions
33 upper arm adjustment facility
34 first torso engaging portion
40 lower sensing arm
41 lower arm main shaft
42 lower rotational sensing protrusions
43 lower arm adjustment facility
44 second torso engaging portion
50 protective cover
52 hook and loop type fasteners
100 sliders
102 finger grips
104 rotational contact extension members
110 cooperating slots
112 oblong opening
114 holding piece
116 battery
118 control unit
200 speaker
202 power source 300 upper flexion sensing adjustment unit
302 lower flexion sensing adjustment unit
304 flexion contact extension members
306 flexion/extension protruding member
400 upper extension sensing adjustment unit
402 lower extension sensing adjustment unit
404 extension contact members It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A back movement monitor and warning device for alerting a user to torso flexion, extension and rotation that exceeds preset parameters comprising:

a) a control box housing having a top wall, a bottom wall, a front wall and a back wall containing adjustment means to set separate upper and lower torso limits of rotation;

b) means comprising a belt surrounding the midsection of said user holding said control box to attach said control box to the user's body;

c) said adjustment means comprising an upper movement sensing arm extending through said top wall of said control box, said upper sensing arm including a first torso engaging portion at an upper end and a pair of upper rotational sensing protrusions at a lower end disposed within said control box;

d) said adjustment means also comprising a lower movement sensing arm extending through said bottom wall of said control box and supported within said control box independently of said upper movement sensing arm, said lower sensing arm including a second torso engaging portion at a lower end and a pair or lower rotational sensing protrusions at an upper end disposed within said control box;

e) adjustable upper rotational contact means disposed such that the user predetermines a limit of upper torso rotational movement independent of lower rotational movement and where, if that upper rotational limit is exceeded, said upper rotational sensing protrusions engage said upper rotational contact means and a rotational warning results;

f) adjustable lower rotational contact means disposed such that the user predetermines a limit of lower torso rotational movement independent of upper rotational movement and where, if that lower rotational limit is exceeded, said lower rotational sensing protrusions engage said lower rotational contact means and a rotational warning results;

g) flexion/extension contact members disposed on both said upper movement sensing arm and said lower movement sensing area;

h) adjustable flexion contact mean disposed such that the user predetermines a limit of torso flexion and where, if that flexion limit is exceeded, said flexion/extension contact members engage said flexion contact means and a flexion warning results; and i) adjustable extension contact means disposed such that the user predetermines a limit of torso extension and where, if that extension limit is exceeded, said flexion/extension contact member engage said extension contact means and an extension warning results.

2. A back movement monitor and warning device as recited in claim 1, wherein said flexion/extension contact members are proximate the distal end of both said upper and lower movement sensing arms relative to said upper and lower body engaging portions.

3. A back movement monitor and warning device as recited in claim 1, wherein said upper movement sensing arm includes telescopic adjustment means.

4. A back movement monitor and warning device as recited in claim 1, wherein said lower movement sensing arm includes telescopic adjustment means.

5. A back movement monitor and warning device as recited in claim 1, wherein said adjustable upper rotational contact means comprises two sliders disposed on said top wall of said control box.

6. A back movement monitor and warning device as recited in claim 1, wherein said adjustable lower rotational contact means comprises two sliders disposed on said bottom wall of said control box.

7. A back movement monitor and warning device as recited in claim 1, wherein said upper movement sensing arm and said lower movement sensing arm both include a biasing means proximate said control box, said biasing means serving to maintain said upper body engaging portion and said lower body engaging portion in substantial contact with the user's torso.

8. A back movement monitor and warning device as recited in claim 1, wherein said rotational warning is an audible generated tone.

9. A back movement monitor and warning device as recited in claim 1, wherein said flexion warning is an audible generated tone.

10. A back movement monitor and warning device as recited in claim 1, wherein said extension warning is an audible generated tone.

* * * * *